(12) United States Patent
Schaefer

(10) Patent No.: US 6,368,319 B1
(45) Date of Patent: Apr. 9, 2002

(54) PEDICLE SCREW

(76) Inventor: Bernd Schaefer, Eggstr. 27, 6315 Oberaegeri (CH)

( * ) Notice: Subject to any disclaimer, the term of this patent is extended or adjusted under 35 U.S.C. 154(b) by 0 days.

(21) Appl. No.: 09/564,850

(22) Filed: May 4, 2000

(30) Foreign Application Priority Data

May 6, 1999 (DE) .......................... 199 22 440

(51) Int. Cl.7 .................. A61F 2/30; F16B 35/04; F16B 21/18
(52) U.S. Cl. .................. 606/60; 606/61; 606/73; 411/412; 411/517; 411/519
(58) Field of Search .................. 606/60, 61, 64, 606/66, 73; 411/353, 400, 412, 519, 518, 517

(56) References Cited

U.S. PATENT DOCUMENTS

| | | | | |
|---|---|---|---|---|
| 1,028,795 A | * | 6/1912 | Steinhouse | |
| 2,470,927 A | * | 5/1949 | Hale, Jr. | |
| 2,485,531 A | * | 10/1949 | Dzus et al. | |
| 2,489,870 A | * | 11/1949 | Dzus | |
| 2,492,115 A | * | 12/1949 | Crowther | |
| 2,929,474 A | * | 3/1960 | Boardman | |
| 3,997,138 A | * | 12/1976 | Crock et al. | |
| 4,041,939 A | * | 8/1977 | Hall | |
| 4,484,570 A | * | 11/1984 | Sutter et al. | |
| 5,232,322 A | * | 8/1993 | Regensburger | |
| 5,690,632 A | * | 11/1997 | Schwartz et al. | 606/73 |

* cited by examiner

Primary Examiner—Jeffrey A. Smith
(74) Attorney, Agent, or Firm—Birch, Stewart, Kolasch & Birch

(57) ABSTRACT

The invention involves a pedicle screw having a screw shaft and a screw head, with a free end of the screw shaft having a holding device for holding a safety mechanism. This safety mechanism serves to keep the pedicle screw from pulling out.

14 Claims, 1 Drawing Sheet

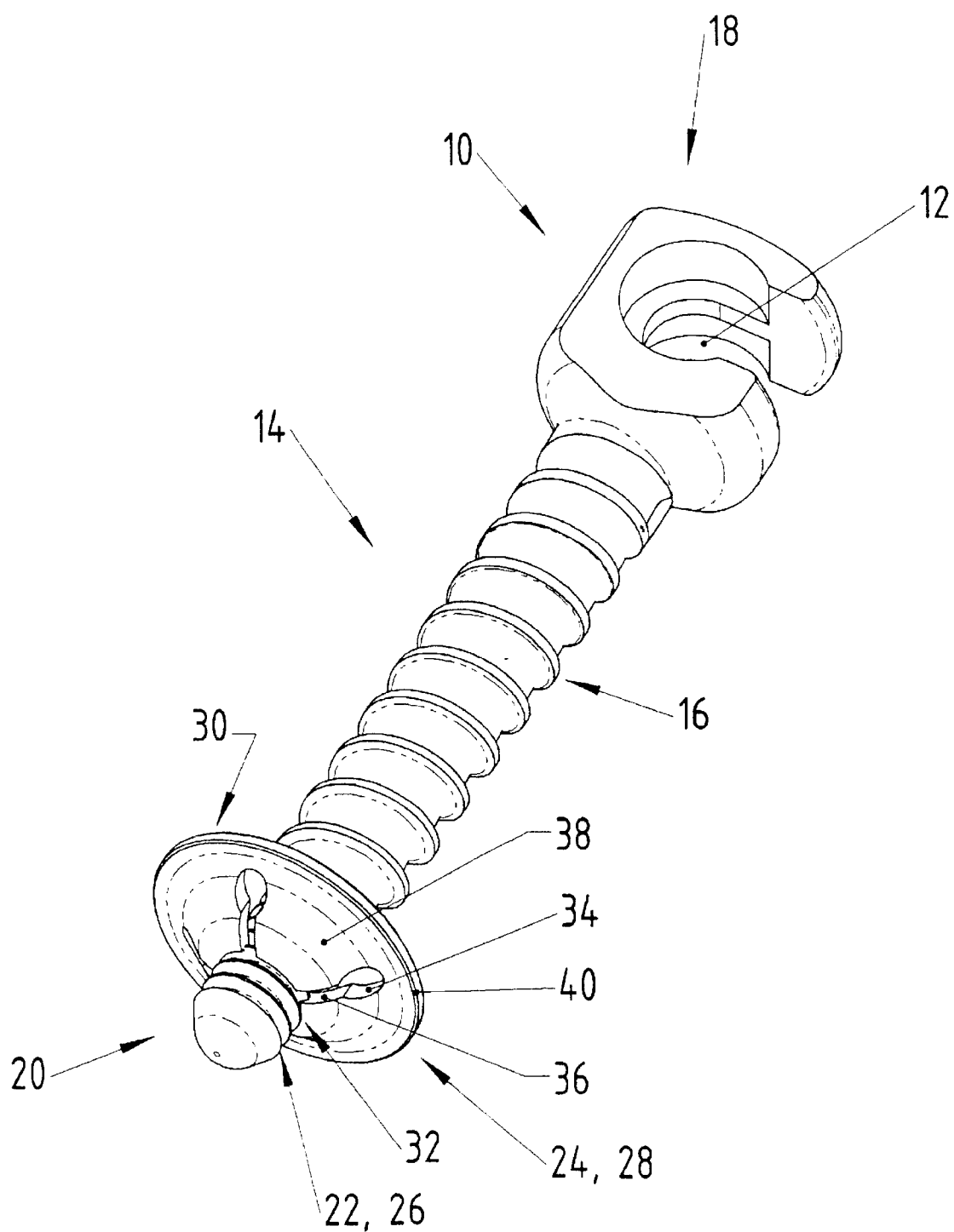

PEDICLE SCREW

BACKGROUND OF THE INVENTION

This application claims a priority based on German patent application 199 22 440.4, filed May 6, 1999, and the contents of that priority application are incorporated herein by reference.

The invention involves a pedicle screw having a threaded screw shaft and a screw head, with the screw head having mechanisms for affixing correction elements.

Pedicle screws are known in many diverse forms. As a rule, a pedicle screw has a screw shaft, whose length and diameter are adapted to a bone diameter and which is threaded so that the pedicle screw can be screwed into the bone in a problem-free and secure manner and, above all, without destroying the bone. The screw head is structured such that correction and/or fixing tabs can be mounted on it in a play-free manner, for achieving osteosynthesis.

It has been shown that for all pedicle screws there is a danger, particularly for persons with osteoporosis, that, although the screws can be screwed into the bone in a problem-free manner, the screws, however, either loosen by themselves or are sometimes even be pulled out of the bone by application of large external forces.

It is thus an object of this invention to provide a pedicle screw of the type mentioned in the opening paragraph above that can be securely anchored in bone and which considerably reduces the danger of its being pulled out.

SUMMARY OF THE INVENTION

According to principles of the invention a free end of a screw shaft of a pedicle screw, of the type mentioned in the opening paragraph above, is equipped with a pull-out prevention device; in particular with a holding device, which is independent of a first threading, for holding a safety mechanism that secures the pedicle screw against unintentional detachment after it is screwed in.

Due to the safety mechanism, which is attached to the free end of the threaded shaft of the inventive pedicle screw once the screw has assumed its final position in the bone, a danger of its being pulled out of the bone is considerably reduced since the pedicle screw is not only supported on the bone, especially on a superior thoracic vertebrae, by threading, but also by the safety mechanism. A side of the safety mechanism lying opposite the screw head rests on the bone and the bone is held between the screw head and the safety mechanism.

In an enhanced embodiment the holding device defines at least one circumferential groove. The safety mechanism is supported in this circumferential groove on the screw shaft and is held securely to the screw shaft in the circumferential groove. The circumferential groove also has the advantage that the safety mechanism can be affixed to the shaft about the entire circumference of the shaft.

An additional enhancement provides that the holding device defines an additional threading. This threading can have a different spacing and/or pitch than the screw-in threading of the screw shaft. As a rule, this additional threading is a machine threading, so that standard parts or safety mechanisms having standardized inner threading can be engaged therewith. In addition, threads of this type are relatively easy to manufacture.

A cost-effective embodiment of the safety mechanism is, for example, a locking washer, which can be manufactured as a stamped part or as a stamped bent part. A locking washer has, in addition, the advantage that it has a large area for resting on the outer surface of the bone, and, in this way, a holding force is optimally distributed.

In a preferred embodiment, the locking washer has an opening for receiving the holding device. A free end of the screw shaft is held in this opening, with dimensions of the opening being selected so that an edge defining the opening lies in the circumferential groove, for example, or in the additional threaded groove.

A simple attachment of the safety mechanism is achieved in that the opening is also open at its edge. In this regard, an edge-opening slit of the opening can have a slightly smaller clearance width than a diameter of the free end of the screw shaft.

In order to be able to optimally oppose load peaks, the safety mechanism is structured to be elastic at a connection area where it is connected with the holding device. In this way, a rigid construction that is susceptible to failure is avoided and the elastic embodiment additionally has the advantage that after overcoming load peaks, the safety mechanism assumes its starting, or rest, position again, by springing back elastically.

In this regard, in a preferred embodiment, the elastic structure can be a bend. For this, the safety mechanism is preferably manufactured from a spring steel.

A preferred additional embodiment provides that the safety mechanism can be clipped, or snapped, onto the holding device. This embodiment allows the safety mechanism to be mounted on the free end of the screw shaft, after the pedicle screw is screwed in, in a relatively simple manner by merely being pressed, or forced, on, such that it preferably self engages with, or snaps onto, the free end of the screw shaft.

In order to achieve a specific elasticity of the safety mechanism, it has one or more slits. Between the slits, bulges, or wings, are provided, which extend, or protrude, radially and have free ends lying on the screw shaft.

An additional embodiment provides that the safety mechanism has openings or holes in which a tool can engage. Using this tool, the safety mechanism can be attached and/or removed. Preferably, a screwing movement is done for accomplishing this.

Preferred materials for the safety mechanism are metals, in particular, spring steel, stainless steel, or titanium, or the safety mechanism is made of resinous plastic or a composite material.

BRIEF DESCRIPTION OF THE DRAWING

The invention is described and explained in more detail below using an embodiment shown in the drawing. The described and drawn features can be used individually or in preferred combinations in other embodiments of the invention. The foregoing and other objects, features and advantages of the invention will be apparent from the following more particular description of a preferred embodiment of the invention, as illustrated in the accompanying drawing. The drawing is not necessarily to scale, emphasis instead being placed upon illustrating principles of the invention in a clear manner.

Additional advantages, characteristics and details are set forth in the following description, with an especially preferred embodiment being described in detail in reference to the drawing. In this regard, the characteristics shown in the drawing and mentioned in the claims and in the description are each inventive individually by themselves or in any desired combination.

The drawing shows a perspective view of the pedicle screw according to the invention with a safety mechanism attached on a free end.

DESCRIPTION OF THE PREFERRED EMBODIMENT

The pedicle screw shown in the drawing has a screw head, indicated by 10, which is constructed as a forked head having an opening 12 that opens on an edge, and a screw shaft 14, which has a first threading 16 by which the pedicle screw 18 is screwed into a bone, especially a superior thoracic vertebra. The screw shaft 14 is equipped on its free end 20 with a holding device, indicated generally by 22, for holding a safety mechanism 24. The free end 22 is constructed, in the depicted embodiment, with a further threading 26, independent from the threading 16, which is preferably a machine threading. The safety mechanism 24, which is formed as a lock, or locking, washer 28, is screwed onto this threading 26. This lock washer 28 has a bearing surface 30 that rests on a vertebra (not shown), and is provided with a central opening 32, through which the free end 20 of the screw shaft 14 is guided. In addition, the lock washer 28 has several holes 34 as well as slits 36 extending radially inwardly to open into the central opening 32. Between the slits 36, bulges, or wings, 38 are formed, which extend radially inwardly from an edge 40 of the lock washer 28. These bulges 38 are bent, or bowed, axially in such a way that a portion thereof lying further radially inwardly has a larger offset from the vertebra (not shown) than does the edge 40, that is, it does not necessarily lie on the vertebra. In this way, a certain elasticity or elastic embodiment of the lock washer 28 is created.

The holes 34 and possibly the slits 36 function for receiving a tool, with which the lock washer 28 can be screwed onto, or off of, the threading 26. There is also the possibility, however, for pressing the lock washer 28 using a tool, for example using pliers or the like, onto the free end 20, so that the lock washer 28 engages with the threading 26. The lock washer 28 affixed onto the threading 26 functions as protection against a pulling out of the pedicle screw 18, so that with it, significantly higher forces can be transferred to the vertebra.

The invention claimed is:

1. A pedicle screw having a screw shaft (14) with a threading (16) and a screw head (10), with the screw head (10) having a mechanism for affixing correcting elements, wherein a free end (20) of the screw shaft (14) has a holding device (22), wherein is further included a safety mechanism (24) attached to said screw shaft by said holding device for securing the pedicle screw from unintentional detachment after it is screwed in, wherein the safety mechanism (24) is structured to be elastic by having an elastic structure at a connection area with the holding device (22), thereby allowing said safety mechanism (24) to be pushed onto said screw shaft.

2. Pedicle screw according to claim 1, wherein the holding device (22) is independent of the threading (16).

3. Pedicle screw according to claim 1, wherein the holding device (22) defines at least one circumferential groove.

4. Pedicle screw according to claims 1 wherein the holding device is an additional threading (26).

5. Pedicle screw according to claim 1, wherein the safety mechanism (24) is a lock washer (28).

6. Pedicle screw according to claim 5, wherein the lock washer (28) has an opening (32) that receives the holding device (22).

7. Pedicle screw according to claim 6, wherein the opening (32) opens on an edge of the lock washer into a radial slit.

8. Pedicle screw as in claim 7, wherein the lockwasher defines at least one opening in which a tool can engage, said opening having a greater breadth than one opening in which a tool can engage, said opening having a greater breadth than said slit.

9. Pedicle screw according to claim 7, wherein the elastic structure is a bend in the lock washer.

10. Pedicle screw according to claim 1, wherein the safety mechanism (24) snaps onto the holding device (22).

11. Pedicle screw according to claim 1, wherein the safety mechanism (24) defines at least one radial slit (36).

12. Pedicle screw according to claim 11, wherein the elastic structure includes axial bulges (38) positioned between slits (36).

13. Pedicle screw according to claim 1, wherein the safety mechanism (24) defines openings (34) in which a tool can engage.

14. Pedicle screw according to claim 1, wherein the safety mechanism (24) is made of one of metal and plastic.

\* \* \* \* \*